(12) United States Patent
Ramstad et al.

(10) Patent No.: US 11,464,595 B2
(45) Date of Patent: Oct. 11, 2022

(54) TELESCOPING MEDICAL DEVICE ASSEMBLY AND STERILE DRAPE

(71) Applicant: INTUITIVE SURGICAL OPERATIONS, INC., Sunnyvale, CA (US)

(72) Inventors: Craig R. Ramstad, Minden, NV (US); Anthony K. McGrogan, San Jose, CA (US); Todd R. Solomon, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 348 days.

(21) Appl. No.: 16/317,280

(22) PCT Filed: Jun. 21, 2017

(86) PCT No.: PCT/US2017/038580
§ 371 (c)(1),
(2) Date: Jan. 11, 2019

(87) PCT Pub. No.: WO2018/013309
PCT Pub. Date: Jan. 18, 2018

(65) Prior Publication Data
US 2019/0223969 A1    Jul. 25, 2019

Related U.S. Application Data

(60) Provisional application No. 62/362,195, filed on Jul. 14, 2016.

(51) Int. Cl.
*A61B 34/30* (2016.01)
*A61B 46/10* (2016.01)
*A61B 17/00* (2006.01)

(52) U.S. Cl.
CPC .............. *A61B 46/10* (2016.02); *A61B 34/30* (2016.02); *A61B 2017/00477* (2013.01); *A61B 2017/00991* (2013.01); *A61B 2034/305* (2016.02)

(58) Field of Classification Search
CPC ... A61B 46/10; A61B 34/30; A61B 2034/305; A61B 2017/00477; A61B 2017/00991
See application file for complete search history.

(56) References Cited

U.S. PATENT DOCUMENTS 6,331,181 B1    12/2001    Tierney et al.
7,331,967 B2    2/2008    Lee et al.
(Continued)

FOREIGN PATENT DOCUMENTS

WO    WO-2015052629 A1    4/2015

OTHER PUBLICATIONS

International Search Report and Written Opinion for Application No. PCT/US2017/038580, dated Oct. 30, 2017, 21 pages.
(Continued)

*Primary Examiner* — Ankit D Tejani
*Assistant Examiner* — Joshua Brendon Solomon
(74) *Attorney, Agent, or Firm* — Jones Robb, PLLC (57) ABSTRACT

A surgical system includes an insertion assembly and a drape shroud assembly mounted on the insertion assembly. When a sleeve of a surgical drape draping the insertion assembly is fastened to the drape shroud assembly, the sleeve is divided into two pockets. Instead of managing one long tube, the management problem of the drape sleeve is reduced to managing a plurality of shorter tubes. Shorter tubes make it easier for excess sleeve material to accordion as the tube length shortens instead of possibly bowing out and contacting a part of the insertion assembly or some other part of the surgical system.

14 Claims, 9 Drawing Sheets

(56) References Cited

U.S. PATENT DOCUMENTS

| | | |
|---|---|---|
| 7,727,244 B2 | 6/2010 | Orban, III et al. |
| 8,220,468 B2 | 7/2012 | Cooper et al. |
| 9,096,033 B2 | 8/2015 | Holop et al. |
| 2009/0248039 A1 | 10/2009 | Cooper et al. |
| 2011/0277775 A1 | 11/2011 | Holop et al. |
| 2015/0133960 A1 | 5/2015 | Lohmeier et al. |
| 2016/0199138 A1 | 7/2016 | Cooper et al. |
| 2017/0333147 A1* | 11/2017 | Bernstein ............... A61B 50/30 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

Fig. 7

TELESCOPING MEDICAL DEVICE ASSEMBLY AND STERILE DRAPE

RELATED APPLICATIONS

This patent application is a U.S. national stage application under 35 U.S.C. § 371(c) of International Application No. PCT/US2017/038580, filed on Jun. 21, 2017, which claims priority to and the filing date benefit of U.S. Provisional Patent Application No. 62/362,195, entitled "TELESCOPING MEDICAL DEVICE ASSEMBLY AND STERILE DRAPE" filed Jul. 14, 2016, each of which is incorporated by reference herein in its entirety.

BACKGROUND

Field of Invention

The present invention relates generally to sterile surgical drapes for computer-assisted surgical systems, and more particularly to apparatuses used in management of a sterile drape during operation of the computer-assisted surgical system.

Description of Related Art

Figure 1:
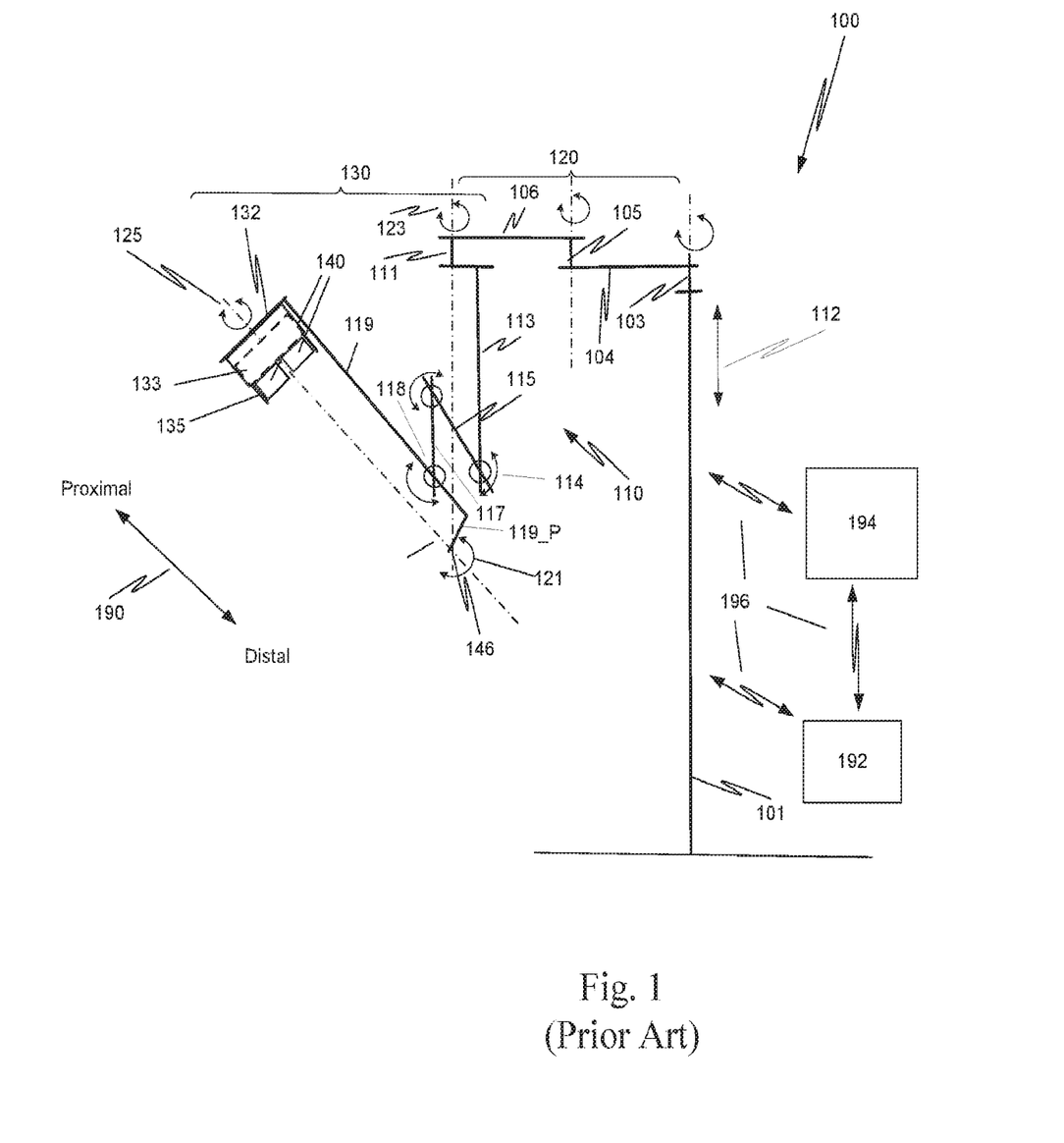
FIG. 1 is an illustration of a prior art computer-assisted surgical system.

A surgical drape has been previously used to cover a surgical manipulator, such as plurality of surgical instrument manipulator assemblies 140 in computer-assisted surgical system 100. The drapes have taken various forms. In each instance, the manipulator and associated support links are covered with a sterile surgical drape prior to the start of the surgical procedure.

Surgical system 100 is a computer-assisted surgical system that includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. Pat. No. 9,060,678 B2 (file Jun. 13, 2007), which is incorporated by reference herein.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 194 also includes a stereoscopic video output display positioned such that images on the display are generally focused at a distance that corresponds to the surgeon's hands working behind/below the display screen. These aspects are discussed more fully in U.S. Pat. No. 6,671,581 (filed Jun. 5, 2002), which is incorporated by reference herein.

Control during insertion of the instruments may be accomplished, for example, by the surgeon moving the instruments presented in the image with one or both of the masters. The surgeon uses the masters to move the instrument in the image side-to-side and to pull or push the instrument towards or away from the surgeon in the image. The motion of the masters commands the imaging system and an associated surgical device assembly to steer towards a fixed center point on the output display and to advance or retract inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

Base 101 of patient side support system 110 supports an arm assembly that includes a passive, uncontrolled setup arm assembly 120 and an actively controlled manipulator arm assembly 130. Actively controlled manipulator arm assembly 130 is referred to as entry guide manipulator 130.

In one example, setup arm assembly 120 includes two passive rotational setup joints 103 and 105. Rotational setup joints 103 and 105 allow manual positioning of coupled setup links 104 and 106 if the joint brakes for setup joints 103 and 105 are released. Alternatively, some of these setup joints may be actively controlled, and more or fewer setup joints may be used in various configurations. Setup joints 103 and 105, and setup links 104 and 106, allow a person to place entry guide manipulator 130 at various positions and orientations in Cartesian x,y,z space. A prismatic setup joint (not shown) between link 104 of setup arm assembly 120 and base 101 may be used for vertical, horizontal, or other linear adjustments 112.

A remote center of motion 146 is a location at which yaw, pitch, and roll axes intersect (i.e., the location at which the kinematic chain remains effectively stationary while joints move through their range of motion). Some of these actively controlled joints are manipulators that are associated with controlling DOFs of individual instruments, and others of these actively controlled joints are associated with controlling DOFs of a single assembly of these manipulators. The active joints and links are movable by motors or other actuators and receive movement control signals that are associated with master arm movements at surgeon's console 194.

As shown in FIG. 1, a manipulator assembly yaw joint 111 is coupled between an end of setup link 106 and a first end, e.g., a proximal end, of a first manipulator link 113. Yaw joint 111 allows first manipulator link 113 to move with reference to link 106 in a motion that may be arbitrarily defined as "yaw" around a manipulator assembly yaw axis 123. As shown, the rotational axis of yaw joint 111 is aligned with remote center of motion 146, which is generally the position at which an instrument enters the patient (e.g., at the umbilicus for abdominal surgery).

In one embodiment, setup link 106 is rotatable in a horizontal (sometimes referred to as x,y) plane, and yaw joint 111 is configured to allow first manipulator link 113 in entry guide manipulator 130 to rotate about yaw axis 123. Setup link 106, yaw joint 111, and first manipulator link 113 provide a constantly vertical yaw axis 123 for entry guide manipulator 130, as illustrated by the vertical line through yaw joint 111 to remote center of motion 146.

A distal end of first manipulator link 113 is coupled to a proximal end of a second manipulator link 115 by a first actively controlled rotational joint 114. A distal end of second manipulator link 115 is coupled to a proximal end of a third manipulator link 117 by a second actively controlled rotational joint 116. A distal end of third manipulator link 117 is coupled to a distal portion of a fourth manipulator link 119 by a third actively controlled rotational joint 118.

In one embodiment, links 115, 117, and 119 are coupled together to act as a coupled motion mechanism. Coupled motion mechanisms are well known (e.g., such mechanisms are known as parallel motion linkages when input and output link motions are kept parallel to each other). For example, if rotational joint 114 is actively rotated, joints 116 and 118 are also actively rotated so that link 119 moves with a constant relationship to link 115. Therefore, it can be seen that the rotational axes of joints 114, 116, and 118 are parallel. When these axes are perpendicular to rotational axis 123 of joint 111, links 115, 117, and 119 move with reference to link 113 in a motion that may be arbitrarily defined as "pitch" around a manipulator assembly pitch axis.

The manipulator pitch axis extends into and out of the page in FIG. 1 at remote center of motion 146, in this aspect. The motion around the manipulator assembly pitch axis is represented by arrow 121. Since links 115, 117, and 119 move as a single assembly, first manipulator link 113 may be considered an active proximal manipulator link, and second through fourth manipulator links 115, 117, and 119 may be considered collectively an active distal manipulator link.

An entry guide manipulator assembly platform 132, sometimes referred to as platform 132, is coupled to a distal end of fourth manipulator link 119. An entry guide manipulator assembly 133 is rotatably mounted on platform 132. Entry guide manipulator assembly 133 includes a surgical instrument manipulator positioning system.

Entry guide manipulator assembly 133 rotates a plurality of surgical instrument manipulator assemblies 140 as a group around axis 125. Specifically, entry guide manipulator assembly 133 rotates as a single unit with reference to platform 132 in a motion that may be arbitrarily defined as "roll" around an entry guide manipulator assembly roll axis 125.

Each of a plurality of surgical instrument manipulator assemblies 140 is coupled to entry guide manipulator assembly 133 by a different insertion assembly 135. In one aspect, each insertion assembly 135 is a telescoping assembly that moves the corresponding surgical instrument manipulator assembly away from and towards entry guide manipulator assembly 133. In FIG. 1, each of the insertion assemblies is in a fully retracted position.

Each of the plurality of surgical instrument manipulator assemblies includes a plurality of motors that drive a plurality of outputs in an output interface of that surgical instrument manipulator assembly. See U.S. Patent Application Publication No. US 2016/0184037 A1 (filed Aug. 13, 2014), which is incorporated by reference, for one example of a surgical instrument manipulator assembly and a surgical instrument that can be coupled to the surgical instrument manipulator assembly.

In one aspect, a membrane interface that is part of a surgical drape may be placed between the instrument mount interface of a surgical instrument manipulator assembly and the input interface of the transmission unit of a corresponding surgical instrument. See, for example, U.S. Patent Application Publication No. US 2011/0277776 A1 (filed Aug. 12, 2010) for an example of the membrane interface and surgical drape. In another aspect, a sterile adapter that is part of a surgical drape may be placed between the instrument mount interface of the surgical instrument manipulator assembly and the input interface of the transmission unit of the corresponding surgical instrument. See, for example, U.S. Patent Application Publication No. US 2011/0277775 A1 (filed Aug. 12, 2010) for an example of a sterile adapter and a surgical drape.

Figure 2:
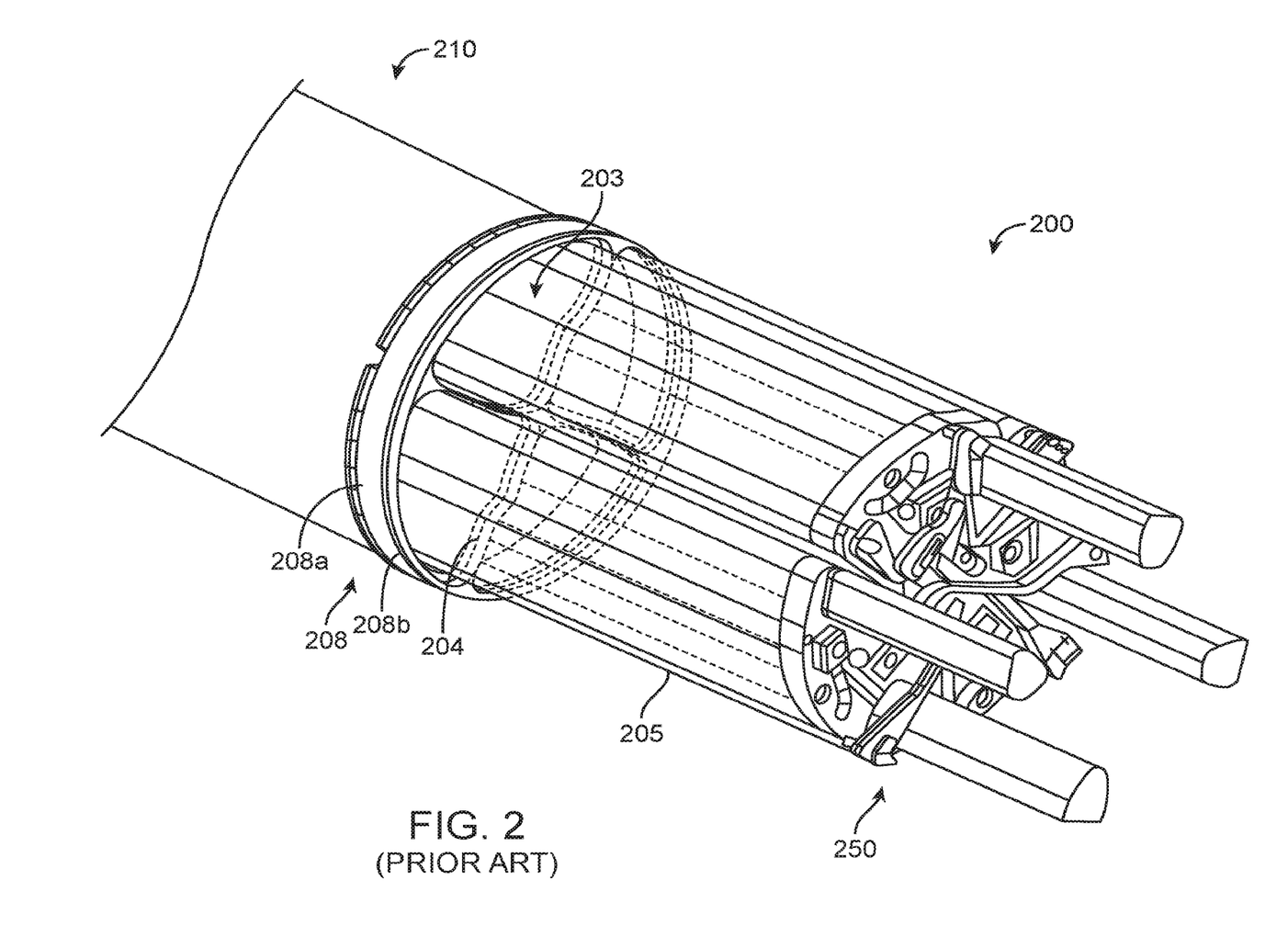
FIG. 2 is a representation of one example of a prior art surgical drape.

FIG. 2 is a perspective view of a drape portion 200 of an extended surgical drape including a sterile adapter 250. Drape portion 200 includes a plurality of drape sleeves 205 coupled between rotatable seal 208 and sterile adapter 250.

Rotatable seal 208 operably couples proximal openings 203 of plurality of drape sleeves 205 to the manipulator platform of the manipulator arm assembly. In one example, rotatable seal 208 includes a rotatable labyrinth seal having a roll cover portion 208a and a base comb portion 208b. Base comb portion 208b is rotatable relative to roll cover portion 208a. Base comb portion 208b includes a disc with ribs 204 that form a plurality of wedge-shaped "frames" with apertures, and each of the frames is sized to circumscribe a surgical instrument manipulator assembly. A proximal end of each of plurality of drape sleeves 205 is coupled to a different one of the plurality of wedge-shaped frames of base comb portion 208b. Ribbed base comb portion 208b aids in draping each individual one of the surgical instrument manipulator assemblies, which are closely clustered on the rotatable base plate of entry guide manipulator assembly 133, and it further aids in maintaining the orientation and arrangement of each of the plurality of drape sleeves 205 as the draped surgical instrument manipulator assemblies move during a surgical procedure.

Although FIG. 2 illustrates each of plurality of drape sleeves 205 in an extended state, for example as the surgical instrument manipulator assemblies extend along their respective insertion assemblies. Each of plurality of drape sleeves 205 may independently retract and extend as a corresponding surgical instrument manipulator assembly is independently and/or dependently controlled with respect to other surgical instrument manipulator assemblies.

Roll cover portion 208a fixedly mounts to frame of manipulator platform 132 (e.g., the manipulator halo) and base comb portion 208b fixedly mounts to the rotatable base plate of entry guide manipulator assembly 133, such that when the rotatable base plate of entry guide manipulator assembly 133 is rotated, base comb portion 208b also rotates in combination with the draped surgical instrument manipulator assemblies. Since the proximal end of each of plurality of drape sleeves 205 is coupled to base comb portion 208b, all the drape sleeves 205 rotate together as a group with reference to a more proximal drape portion 210.

SUMMARY

A surgical system includes an insertion assembly and a drape shroud assembly mounted on the insertion assembly. When a sleeve of a surgical drape draping the insertion assembly is fastened to the drape shroud assembly, the sleeve is divided into two pockets. Instead of managing one rather long tube, the management problem of the drape sleeve is reduced to managing a plurality of shorter tubes. Shorter tubes make it easier for excess sleeve material to accordion as the tube length shortens instead of possibly bowing out and contacting a part of the insertion assembly or some other part of the surgical system. In one aspect, the surgical system includes the surgical drape.

In one aspect, the insertion assembly includes a telescoping assembly. The telescoping assembly has a first portion and a second portion. The second portion has a first end and a second end. The second end of the second portion is coupled to the first portion to move the second portion.

The drape shroud assembly has a first end and a second end. The drape shroud assembly is coupled to the second portion of the telescoping assembly so that the first end of the second portion is adjacent a first end of the drape shroud assembly. A body of the drape shroud assembly extends between the first end and the second end of the drape shroud assembly. A plurality of tabs extends from the second end of the drape shroud assembly.

In yet a further aspect, the surgical system includes a surgical instrument manipulator assembly coupled to the insertion assembly. The surgical instrument manipulator assembly includes an insertion assembly guard. The insertion assembly guard extends from a side of the surgical instrument manipulator assembly attached to the insertion assembly, and the insertion assembly guard is configured to extend around a portion of the insertion assembly.

Thus, the drape shroud assembly includes a body having a first end and a second end, an outer surface extending between the first end and the second end, and an inner surface extending between the first end and the second end. The inner surface of the body bounds an inner volume. The inner volume is sized to permit at least part of the insertion assembly to be contained within the inner volume. The body is configured for attachment to the insertion assembly. A plurality of tabs extends from the second end of the body.

A method includes managing a sleeve of a sterile drape surrounding an insertion assembly by configuring the sleeve as a plurality of pockets. The act of configuring the sleeve as a plurality of pockets includes attaching the sleeve to a drape shroud assembly mounted on the insertion assembly.

BRIEF DESCRIPTION OF THE DRAWINGS

In the drawings, the first digit in a three-digit reference numeral of an element is the number of the figure in which that element first appears.

DETAILED DESCRIPTION

In one aspect, management of a drape sleeve 305 of a sterile surgical drape is enhanced by attaching drape sleeve 305 to insertion assembly 135 using an attachment element 325. This effectively divides a drape sleeve into two parts—a first pocket part 305a and a second pocket part 305b (FIGS. 3A and 3B); i.e., the single tube of drape sleeve 305 is subdivided into a plurality of tubes. In this aspect, drape sleeve 305 extends from a mechanical interface element 350 around surgical instrument manipulator assembly 140 and around insertion assembly 135 to a portion of a rotatable seal mounted on entry guide manipulator assembly platform 132.

Figure 3A:
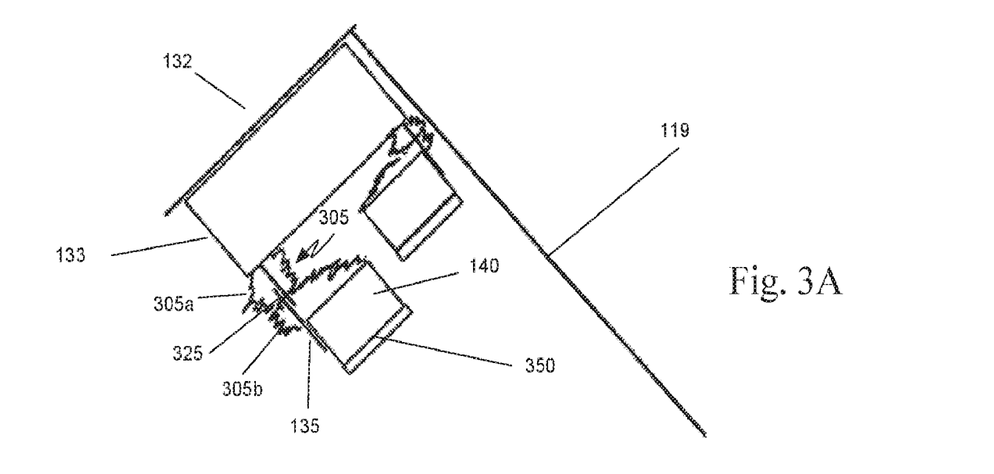
FIGS. 3A and 3B show an insertion assembly in different states with a sleeve draping the insertion assembly attached to an attachment element on the insertion assembly to divide the sleeve into a plurality of pockets for better drape management.
Figure 3B:
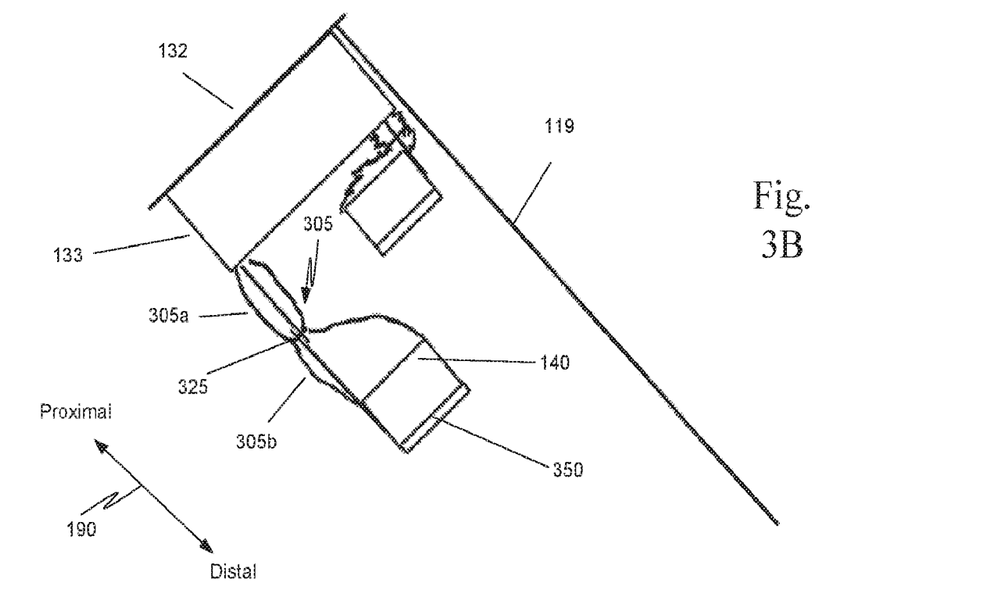

In the system of FIG. 2, drape sleeve 205 was managed as a whole as a surgical instrument manipulator assembly was moved distally (e.g., moved in a first direction) and proximally (e.g., moved in a second direction opposite to the first direction). In contrast, configuring sleeve 305 to have a plurality of pocket parts makes management of sleeve 305 easier and reduces the likelihood that sleeve 305 is caught or snagged as surgical instrument manipulator assembly 140 is moved in the first and second directions.

Instead of managing one rather long tube, as in FIG. 2, the management problem is reduced to managing a plurality of shorter tubes. Shorter tubes make it easier for excess sleeve material to accordion as the tube length shortens instead of possibly bowing out and contacting a part of insertion assembly 135 or some other part of the surgical system.

In the examples of FIGS. 3A and 3B, at least one sleeve of a plurality of sleeves of a surgical system drape is subdivided into two pocket parts by attaching the or each sleeve to an insertion assembly associated with that sleeve. The attachment point to insertion assembly 135 is selected so that that the attachment does not result in sleeve 305 being caught or snagged by insertion assembly 135 at the location of the attachment, and so that the proximal and distal movement of insertion assembly 135 is not hindered by the attachment.

The subdivision of drape sleeve 305 into two pocket parts is illustrative only and is not intended to be limiting. In other aspects, drape sleeve 305 can be subdivided into more than two pocket parts by using more than one attachment location on insertion assembly 135. The number of pocket parts in plurality of pocket parts is selected to facilitate surgical drape sleeve management.

In another aspect, to further facilitate management of a drape sleeve 405, a drape shroud assembly 420 (FIGS. 4A and 4B) is mounted on an insertion assembly 135 of computer assisted surgical system 100 to create a medical device insertion assembly. In this aspect, drape sleeve 405 extends from a mechanical interface element 450 around surgical instrument manipulator assembly 140, around drape shroud assembly 420, and around insertion assembly 135 to a portion of a rotatable seal. Unlike, the prior system illustrated in FIG. 2, as surgical instrument manipulator assembly 140 is moved distally and proximally by insertion assembly 135 (i.e., moved in the first direction and in the second direction), drape shroud assembly 420 prevents drape sleeve 405 from being entangled in the mechanism of insertion assembly 135. This assures not only the integrity of the sterile barrier, it also assures that the surgical procedure is not hampered by drape sleeve 405 being caught in insertion assembly 135.

Figure 4A:
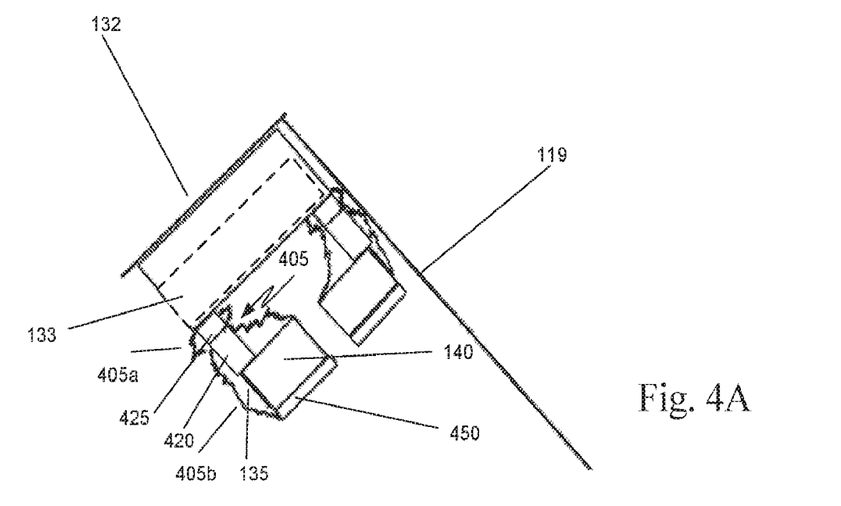
FIGS. 4A and 4B show an insertion assembly in different states with a sleeve draping the insertion assembly attached to a drape shroud assembly, mounted on the insertion assembly, to divide the sleeve into a plurality of pockets for better drape management.
Figure 4B:
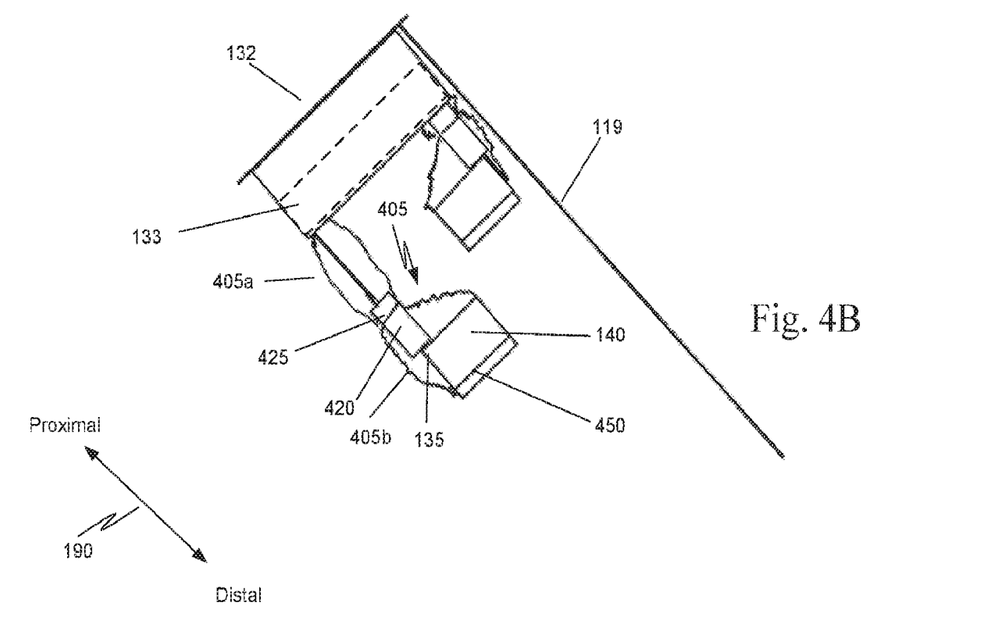

In one aspect, drape shroud assembly 420 is mounted to insertion assembly 135. A distal portion of insertion assembly 135 is at least partially surrounded by drape shroud assembly 420. Enough of insertion assembly 135 is surrounded by drape shroud assembly 420 so that drape shroud assembly 420 prevents drape sleeve 405 from interacting with the distal portion of insertion assembly 135 as insertion assembly 135 moves surgical instrument manipulator assembly 140 in a proximal direction and in a distal direction. In one aspect, drape shroud assembly 420 has a shape that prevents drape sleeve 405 from interacting with any part of insertion assembly 135.

In one aspect, drape sleeve 405 is affixed to drape shroud assembly 420 at a drape tie-down region 425 so that drape sleeve 405 is divided into a first drape sleeve portion 405a and a second drape sleeve portion 405b. The division of drape sleeve into two separate portions, sometimes called pockets, alleviates the bulk that must be collapsed and extended as surgical instrument manipulator assembly 140 is moved proximally and distally by insertion assembly 135. Thus, further reduces the likelihood that drape sleeve 405 becomes entangled in insertion assembly 135.

In this example, drape shroud assembly 420 includes a body having a first end and a second end. An outer surface of the body of drape shroud assembly 420 extends between the first end and the second end. An inner surface of the body of drape shroud assembly 420 also extends between the first end and the second end. The inner surface of the body bounds an inner volume. The inner volume is sized to permit at least part of insertion assembly 135 to be contained within the inner volume, and the body is configured for attachment to the insertion assembly 135. In one aspect, a plurality of tabs extend from the second end of the body. A drape attachment region of drape shroud assembly 420 is defined, in one aspect, by an indentation in the outer surface of the body.

Figure 5A:
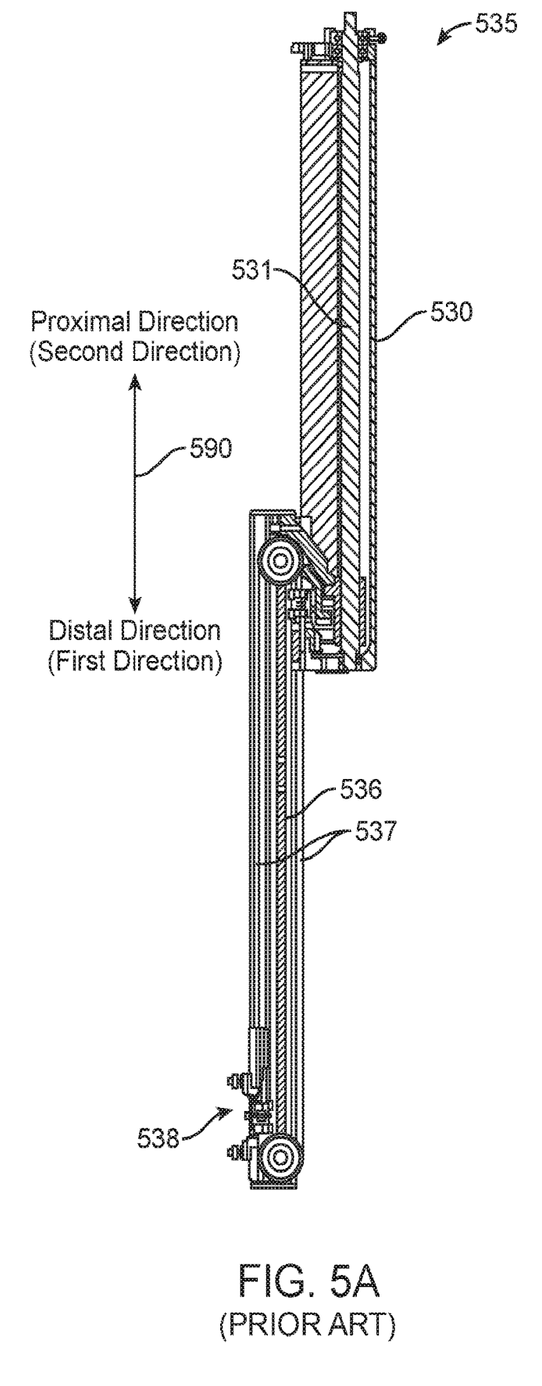
FIG. 5A is an illustration of a prior art insertion assembly.
Figure 5B:
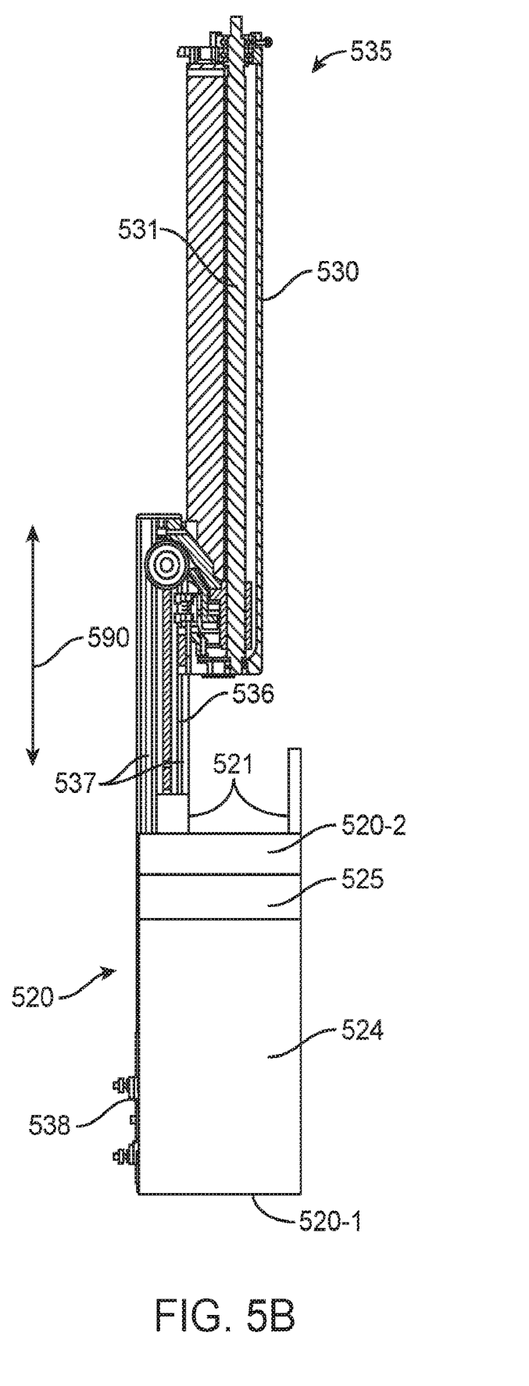
FIG. 5B shows a drape shroud assembly attached to the insertion assembly of FIG. 5A.

To further consider the aspects of a drape shroud assembly, FIG. 5A illustrates one insertion assembly 535 suitable for use with drape shroud assembly 520 (FIG. 5B). Insertion assembly 535 is a telescoping insertion assembly that includes a frame 530, a mid-carriage 536, and a distal carriage 538. Mid-carriage 536 rides on a ball screw 531 in frame 530. In one aspect, ball screw 531 has a 6 mm pitch and so is back-drivable. Mid-carriage 536 includes a metal belt 537 that drives distal carriage 538. Distal carriage 538 is attached to a housing of a surgical instrument manipulator assembly. In one aspect, distal carriage 538 moves twice as far as mid-carriage 536.

Frame 530 and ball screw 531 together are an example of a first portion of an insertion assembly. Mid-carriage 536 and distal carriage 538 are an examples of a second portion and a third portion, respectively, of insertion assembly 535.

FIG. 5B shows drape shroud assembly 520 affixed to insertion assembly 535. In this aspect, drape shroud assembly 520 is attached to a middle portion of insertion assembly 535 (i.e., mid-carriage 536) by screws. In more general terms for dividing a drape sleeve into two pockets with a telescoping assembly having a plurality of portions, the drape shroud assembly is attached to a middle portion of the plurality of portions. This divides the drape sleeve into two more manageable length pockets.

A first end 520-1 of a body 524 of drape shroud assembly 520 is adjacent a first end (distal end) of mid-carriage 536. Body 524 of drape shroud assembly 520 extends in a second direction (proximally) from first end along mid-carriage 536 to a second end (proximal end) 520-2. The first and second directions are shown by arrow 590.

Extending from second end 520-2 of body 524 of drape shroud assembly 520 is a plurality of tabs 521. Plurality of tabs 521, in one aspect, includes three tabs that are a part of drape shroud assembly 520. The number of tabs in plurality of tabs 521 and the size of individual tabs are selected so that as insertion assembly 535 retracts into the base, plurality of tabs 521 does not interfere with the nesting of insertion assembly 535 or with other parts in the base. If there is not an interference problem, the proximal end of drape shroud assembly 520 can be solid. The size and shape of each of plurality of tabs 521 help guide the sleeve of the surgical drape around frame 530 as insertion assembly 535 moves in the first and second directions (i.e., moves in distal and proximal directions) as represented by arrow 590.

Drape shroud assembly 520 includes an inner volume that is bounded by the inner surface of the body of drape shroud assembly 520. As distal carriage 538 is moved towards a most proximal position, which was referred to above as the fully withdrawn position, distal carriage 538 and mid-carriage 536 slide by frame 530, and so drape shroud assembly 520 surrounds frame 530 such that frame 530 is in the inner volume of drape shroud assembly 520.

Adjacent second end 520-2 of body 524 of drape shroud assembly 520 is a drape tie-down region 525. This region helps identify where the sleeve of the surgical drape should be secured to drape shroud assembly 520 so that appropriately sized sub-pockets are formed in the surgical drape to facilitate automatic drape management as insertion assembly 535 moves proximally and distally. In one aspect, drape tie-down region 525 is an indented region in body 524 of drape shroud assembly 520. Alternatively, drape tie-down region 525 could be identified in various ways, such as with a differently colored region of body 524, two lines on the outer surface of body 524, a different surface texture, or any combination of such features.

The vertical length of drape shroud assembly 520 is selected so that when insertion assembly 535 is in the fully withdrawn position, none of plurality of tabs 521 and second end 520-2 contact either the rotatable part of the rotatable seal to which the drape sleeve is attached or contact entry guide manipulator assembly 133, but drape shroud assembly 520 prevents the sleeve of the surgical drape from being snagged or engaged by entry guide manipulator assembly 133.

FIGS. 6A, 6B, 6C, and 6D are more detailed illustrations of one example of an insertion assembly 635, a drape shroud assembly 620, and a surgical instrument manipulator assembly 640. Insertion assembly 635 is the same as insertion assembly 535, and so includes a frame 630 with a ball screw upon which mid-carriage 536 is mounted. Belt 637 in mid-carriage 636 drives a distal carriage to which the housing of surgical instrument manipulator assembly 640 is attached. Drape shroud assembly 620 is attached to mid-carriage 636 in the same way as described above for drape shroud assembly 520.

Insertion manipulator 640 includes a housing that is attached to the distal carriage of insertion assembly 635. The housing of insertion assembly 640 includes an insertion assembly guard 645 that forms a part of the housing of surgical instrument manipulator assembly 640. Insertion assembly guard 645 extends from the side of the housing to which the distal carriage of insertion assembly 635 is attached, and partially surrounds a portion of insertion assembly 635. An inner surface of insertion assembly guard 645 in combination with the wall of the housing of surgical instrument manipulator assembly 640 that abuts insertion assembly 635 defines an opening 646 that surrounds both drape shroud assembly 620 and insertion assembly 635, when insertion assembly 635 is in the fully extended position. In addition, when insertion assembly 635 is in the fully retracted position, insertion assembly guard 645 keeps the distal end of the drape sleeve open so that drape shroud assembly 620 does not snag the drape sleeve.

In one aspect, surgical instrument manipulator assembly 640 includes a drive unit and a drive output assembly. The drive output assembly is coupled to the drive unit. The drive output assembly includes a low backlash coupler coupled to the drive unit. A drive output disk is coupled to the low backlash coupler.

A sterile adapter 650 (FIG. 6A), which is a mechanical interface element, is mounted on the distal face of surgical instrument manipulator assembly 640. A boot of a sterile surgical drape, for example boot 763-1 of sterile surgical drape 760, is affixed to sterile adapter 650 and extends in the proximal direction around the housing of surgical instrument manipulator assembly 640. (An illustration of an example of a sterile surgical drape 760 is presented in FIG. 7.) The boot of the sterile surgical drape, in one aspect, extends to the proximal end of surgical instrument manipulator assembly 640 and around the housing including insertion assembly guard 645. A sleeve of the sterile surgical drape is affixed to a proximal end of the boot and extends from the proximal end of the boot to a rotatable part of the rotatable seal. The sleeve of the sterile surgical drape is attached to drape tie-down region 625 of drape shroud assembly 620 using a tie-down.

Figure 6A:
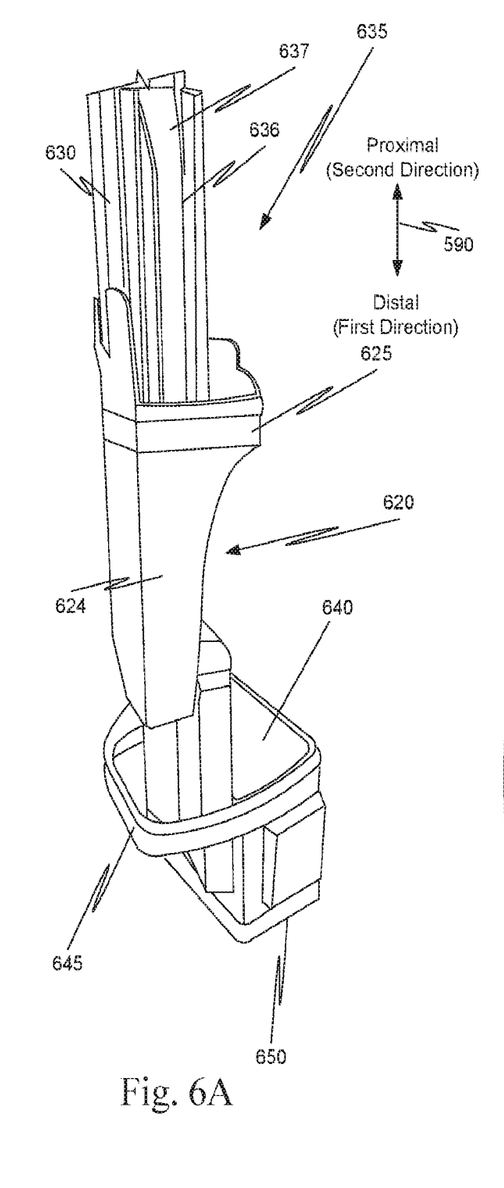
FIGS. 6A, 6B, 6C, and 6D are more detailed illustrations of one example of an insertion assembly, a drape shroud assembly, and a surgical instrument manipulator assembly.
Figure 6B:
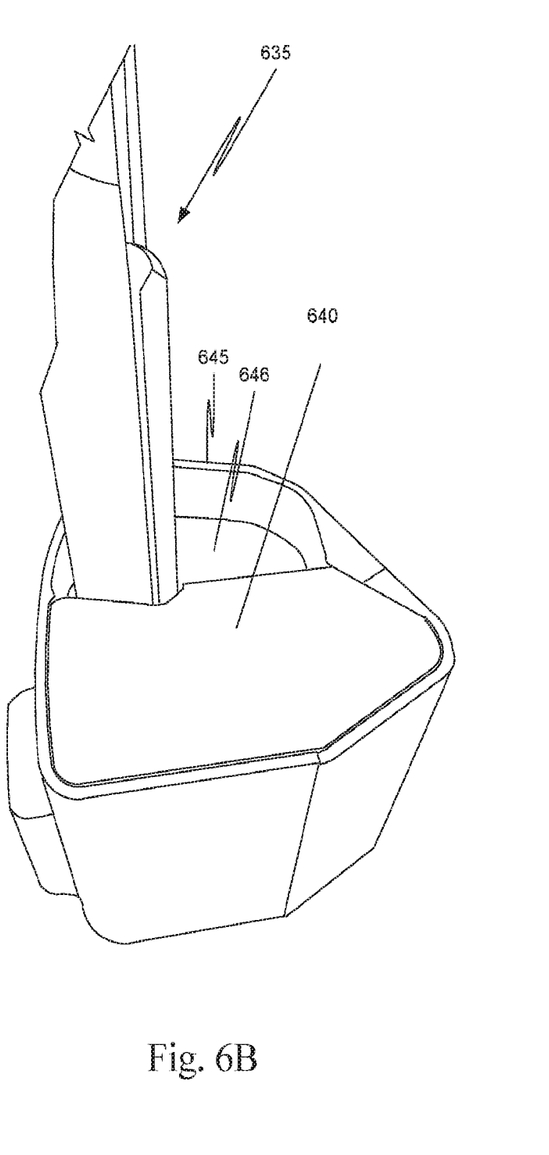

In one aspect, during assembly of the surgical drape, a template is used to position a polyester strap on the drape sleeve, and the polyester strap is attached to the drape sleeve using double-sided pressure-sensitive tape. The polyester strap has hook and loop fabric attached to it so that the size of the polyester strap can be adjusted as necessary to strap the drape sleeve to drape tie-down region 625. An example of hook fabric and loop fabric is a nylon fastening tape consisting of two strips of nylon fabric, one having tiny hooked threads and the other having a coarse looped surface. The two strips form a strong bond when pressed together. One example of a commercially available fastening tape is VELCRO® fastening tape. (VELCRO® is a registered trademark of Velcro Industries B.V.)

Figure 6C:
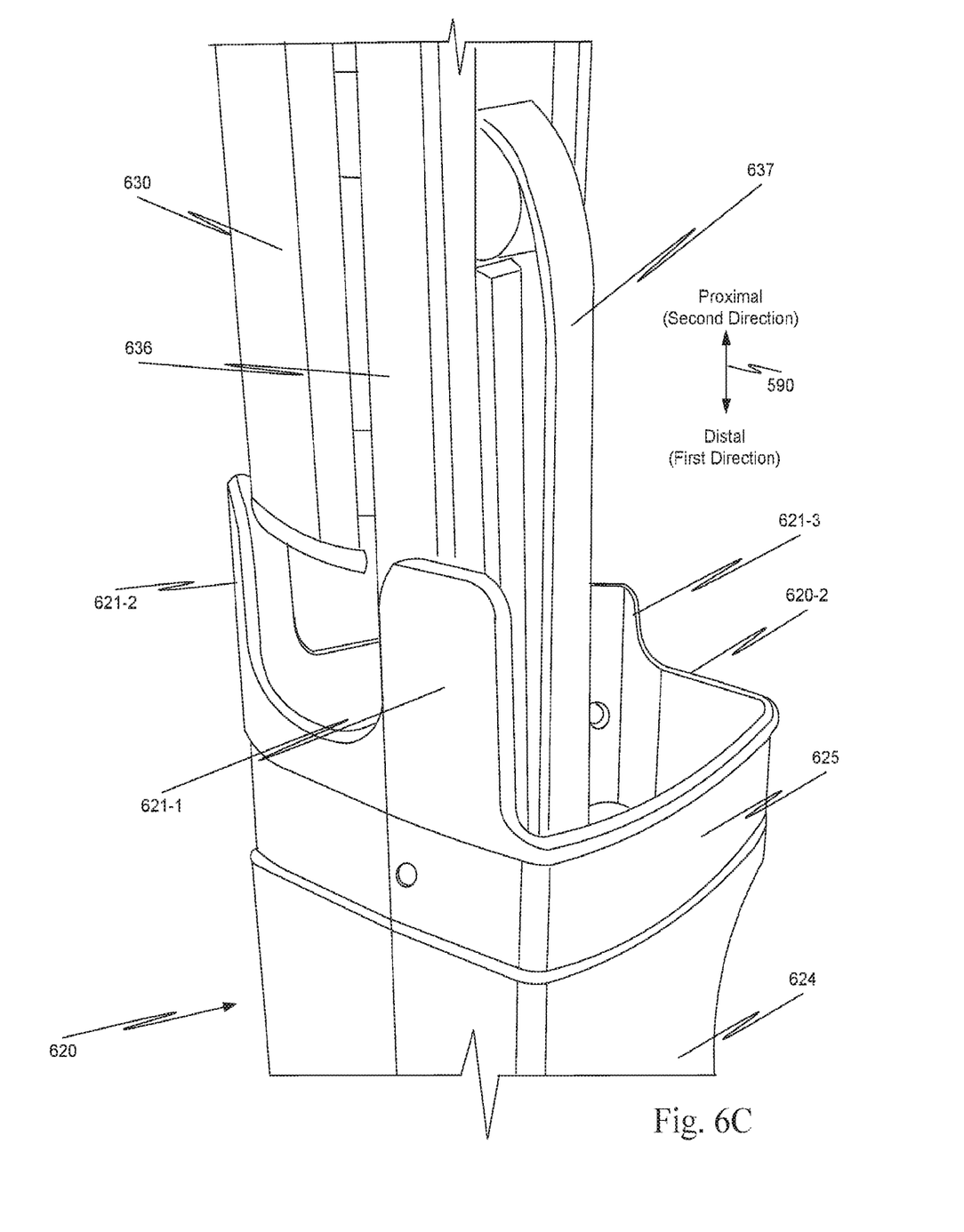
Figure 6D:
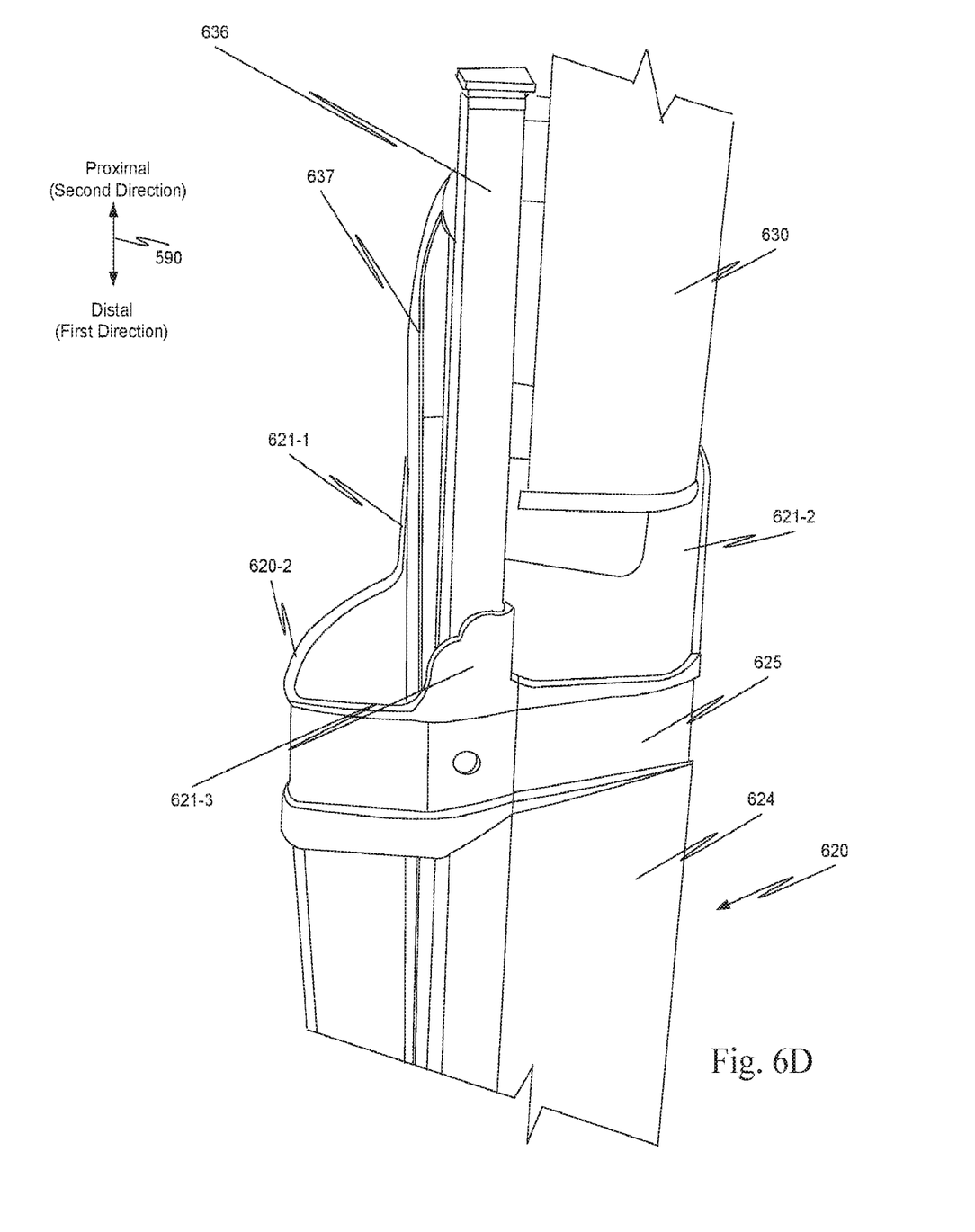

FIGS. 6C and 6D are opposing oblique side views of the proximal portion of drape shroud assembly 620. FIGS. 6C and 6D illustrate one example of plurality of tabs 621-1, 621-2, 621-3 extending in the proximal direction from proximal end 620-2 of body 624 of drape shroud assembly 620.

In one embodiment, surgical drape 760 includes a first portion 761 (FIG. 7) configured to cover platform 132, links 113, 115, 117, and 119, and the associated joints. First portion 761 includes an exterior sterile surface and an interior surface. The interior surface is configured to be positioned adjacent to platform 132, links 113, 115, 117, and 119, and the associated joints. First portion 761 is affixed to a stationary portion of rotatable seal 765, such as a roll cover portion of a rotatable labyrinth seal.

Figure 7:
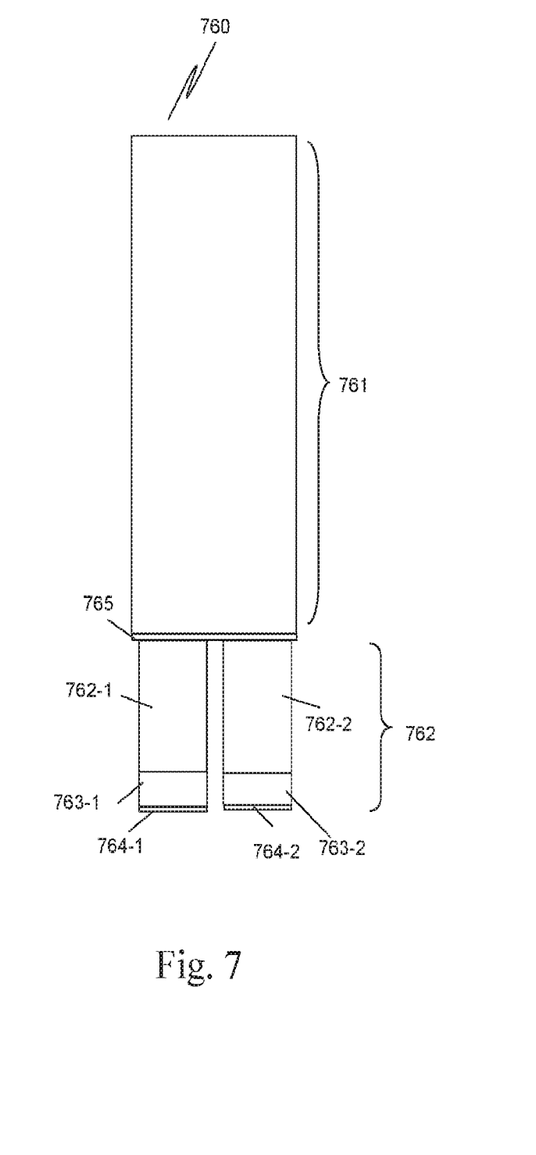
FIG. 7 is a representation of a surgical drape.

A second portion 762 of surgical drape 760 includes a plurality of drape sleeves 762-1 to 762-4 (drape sleeves 762-3, and 762-4 are not visible in FIG. 7), with each drape pocket including at a distal end a boot and a sterile adapter (only boots 763-1, 763-2 and sterile adapters 764-1, 764-2 are visible in FIG. 7). Each sterile adapter includes a mechanical interface configured to mate between the instrument mount interface of a respective surgical instrument manipulator assembly and the input interface of the transmission unit of the corresponding surgical instrument.

A rotating portion of rotatable seal 765, such as a base comb portion of a rotating labyrinth seal, is coupled to a proximal opening of each of plurality of drape sleeves 762-1 to 762-4 to allow all of the drape sleeves to rotate together as a group with reference to more proximal first portion 761 of surgical drape 760. See U.S. Patent Application Publication No. US 2011/0277775 A1 for an example of a suitable surgical drape and rotatable seal.

In one aspect, first portion of 761 of surgical drape 760 and the plurality of drape sleeves are made of a polyethylene material such as ethylene methyl acrylate, commonly referred to as "EMA." In one aspect, each of the plurality of boots is made from low-density polyethylene (LDPE).

As used herein, "first", "second", "third", etc. are adjectives used to distinguish between different components or elements. Thus "first", "second", and "third" are not intended to imply any ordering of the components or elements or to imply any total number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

We claim:

1. A surgical system comprising:
a surgical instrument manipulator comprising an instrument mount interface configured to removably couple a surgical instrument to the surgical instrument manipulator;
an insertion assembly coupled to the surgical instrument manipulator, the insertion assembly being moveable between retracted and extended configurations to move the surgical instrument manipulator in proximal and distal directions; and
a drape shroud assembly mounted on the insertion assembly, the drape shroud assembly comprising a drape shroud body; and
a tubular sterile drape sleeve extending from a distal end portion of the insertion assembly to a proximal end portion of the insertion assembly, the sterile drape sleeve being coupled to the drape shroud body at a middle region of the tubular sterile drape sleeve;
wherein the sterile drape sleeve is coupled to the insertion assembly by the drape shroud body at a location between the proximal end portion and the distal end portion of the insertion assembly, and
wherein a first sleeve portion of the sterile drape sleeve extends proximally from the drape shroud body and at least partially covers at least the proximal end portion of the insertion assembly, and a second sleeve portion of the sterile drape sleeve extends distally from the drape shroud body, at least partially covers at least the distal end portion of the insertion assembly, and is attachable to the surgical instrument manipulator at the instrument mount interface.

2. The surgical system of claim 1, wherein:
the insertion assembly comprises a frame portion comprising the proximal end portion of the insertion assembly and a carriage portion;
the carriage portion comprises a first end comprising the distal end portion of the insertion assembly and a second end opposite the first end;
the surgical instrument manipulator is coupled to the first end of the carriage portion; and
the second end of the carriage portion is movably coupled with the frame portion to move the surgical instrument manipulator between the retracted and extended configurations.

3. The surgical system of claim 2, wherein:
the carriage portion comprises a mid-carriage comprising the second end of the carriage portion and a distal carriage comprising the first end of the carriage portion; and
the distal carriage is movably coupled with the mid-carriage to move the distal carriage in the proximal and distal directions relative to the mid-carriage.

4. The surgical system of claim 2, wherein:
the drape shroud body comprises a first end and a second end opposite the first end;
the drape shroud body is coupled to the carriage portion of the insertion assembly; and
the first end of the carriage portion of the insertion assembly is adjacent the first end of the drape shroud body.

5. The surgical system of claim 1, further comprising:
a surgical instrument coupled to the surgical instrument manipulator.

6. The surgical system of claim 1, wherein:
the surgical instrument manipulator comprises an insertion assembly guard extending from a side of the surgical instrument manipulator coupled to the insertion assembly; and
the insertion assembly guard extends around a portion of the insertion assembly.

7. The surgical system of claim 6, wherein the insertion assembly guard defines an opening surrounding the insertion assembly and the drape shroud assembly.

8. The surgical system of claim 1, wherein the drape shroud body comprises a first end and a second end, wherein a plurality of tabs extend from the second end.

9. The surgical system of claim 8, wherein the plurality of tabs are configured to guide the first sleeve portion of the sterile drape sleeve around the insertion assembly as the insertion assembly moves to the retracted configuration to move the surgical instrument manipulator in the proximal direction.

10. The surgical system of claim 1, further comprising one or more features on the drape shroud body configured to removably attach the sterile drape sleeve to the drape shroud body.

11. The surgical system of claim 1, further comprising an insertion assembly guard coupled with the surgical instrument manipulator, the insertion assembly guard partially surrounding a portion of the insertion assembly and configured to hold a distal end of the second sleeve portion of the sterile drape sleeve open.

12. A method for forming a sterile field around a manipulator of a surgical system, the manipulator comprising an instrument mount interface configured to removably couple a surgical instrument to the manipulator, the method comprising:
attaching a drape shroud assembly to an insertion assembly of a surgical system, the insertion assembly being moveable between retracted and extended configurations and operably coupled to the manipulator of the surgical system to move the manipulator in proximal and distal directions; and
attaching a tubular sterile drape sleeve to the drape shroud assembly and extending the tubular sterile drape sleeve from a proximal end portion of the insertion assembly to a distal end portion of the insertion assembly, wherein the tubular sterile drape sleeve is attached to the drape shroud assembly at a middle region of the tubular sterile drape sleeve, wherein a first sleeve portion of the sterile drape sleeve extends proximally from the drape shroud assembly and a second sleeve portion of the sterile drape sleeve extends distally from the drape shroud assembly,
coupling the drape shroud assembly to the insertion assembly at a location between the proximal end portion and the distal end portion of the insertion assembly,
at least partially covering at least the proximal end portion of the insertion assembly with the first sleeve portion, and
at least partially covering the distal end portion of the insertion assembly and the manipulator with the second sleeve portion and attaching the second sleeve portion to the instrument mount interface of the manipulator.

13. The system of claim 1, wherein a distal end of the second sleeve portion of the drape sleeve comprises a membrane interface configured to be located between the surgical instrument manipulator and an input interface of a surgical instrument coupled to the surgical instrument manipulator.

14. The system of claim 1, wherein a distal end of the second sleeve portion of the drape sleeve comprises a sterile adaptor configured to be located between the surgical instrument manipulator and an input interface of a surgical instrument coupled to the surgical instrument manipulator.

* * * * *